(12) United States Patent
Duerig et al.

(10) Patent No.: US 6,503,271 B2
(45) Date of Patent: Jan. 7, 2003

(54) INTRAVASCULAR DEVICE WITH IMPROVED RADIOPACITY

(75) Inventors: Thomas Duerig, Fremont, CA (US); Mark L. Mathis, Fremont, CA (US); Alan Roy Pelton, Fremont, CA (US); Dieter Stoeckel, Los Altos, CA (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/731,957

(22) Filed: Dec. 7, 2000

(65) Prior Publication Data

US 2001/0001317 A1 May 17, 2001

Related U.S. Application Data

(63) Continuation-in-part of application No. 09/005,401, filed on Jan. 9, 1998, now Pat. No. 6,129,755.

(51) Int. Cl.$^7$ .................................................. A61F 2/06
(52) U.S. Cl. ...................................... 623/1.15; 623/1.34
(58) Field of Search ............................... 623/1.15, 1.34

(56) References Cited

U.S. PATENT DOCUMENTS

| | | | |
|---|---|---|---|
| 3,585,707 A | 6/1971 | Stevens | |
| 4,655,771 A | 4/1987 | Wallsten | |
| 4,665,905 A | 5/1987 | Brown | |
| 4,733,665 A | 3/1988 | Palmaz | |
| 4,925,445 A | 5/1990 | Sakamoto et al. | |
| 5,045,072 A | 9/1991 | Castillo et al. | |
| 5,254,107 A | 10/1993 | Soltesz | |
| 5,632,771 A | 5/1997 | Boatman et al. | |
| 5,725,572 A | 3/1998 | Lam et al. | |
| 5,741,327 A | 4/1998 | Frantzen | |
| 5,800,526 A | 9/1998 | Anderson et al. | |
| 5,824,042 A | * 10/1998 | Lombardi et al. | 623/1.34 |
| 6,022,374 A | 2/2000 | Imran | |
| 6,129,755 A | * 10/2000 | Mathis et al. | 623/1.15 |
| 6,203,569 B1 | * 3/2001 | Wijay | 623/1.15 |
| 6,231,598 B1 | * 5/2001 | Berry et al. | 623/1.15 |
| 6,293,966 B1 | * 9/2001 | Frantzen | 623/1.15 |
| 6,315,790 B1 | * 11/2001 | Gerberding et al. | 623/1.11 |

FOREIGN PATENT DOCUMENTS

WO    WO 97/33534 A1    9/1997

* cited by examiner

Primary Examiner—David H. Willse
Assistant Examiner—Suzette J. Jackson
(74) Attorney, Agent, or Firm—Carl J. Evens

(57) ABSTRACT

A stent having marker tabs formed from a micro-alloyed combination of materials provides for more precise placement and post-procedural visualization in a vessel, by increasing the radiopacity of the stent under X-ray fluoroscopy. A unique micro-alloying process is utilized to form the tabs, comprising a first alloy and a second alloy, wherein one of these alloys is radiopaque. This substantially eliminates the possibility of galvanic action between the tab and the stent. This process is also applicable to other medical devices.

9 Claims, 9 Drawing Sheets

INTRAVASCULAR DEVICE WITH IMPROVED RADIOPACITY

RELATED APPLICATION

This application is a continuation-in-part application of Applicant's co-pending application, Ser. No. 09/005,401, now U.S. Pat. No. 6,129,755, filed Jan. 9, 1998, entitled "An Intravascular Stent Having an Improved Strut Configuration".

BACKGROUND

1. Field of the Invention

The present invention relates to expandable intraluminal grafts ("stents"), and more particularly to expandable intraluminal grafts incorporating tabs for increasing the radiopacity thereof. The present invention also relates to increasing the radiopacity of other medical devices.

2. Discussion of Related Art

Percutaneous transluminal angioplasty (PTA) is a therapeutic medical procedure used to increase blood flow through an artery. In this procedure, the angioplasty balloon is inflated within the stenosed vessel, or body passageway, in order to shear and disrupt the wall components of the vessel to obtain an enlarged lumen. With respect to arterial stenosed lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or completely block the lumen. Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct the problem.

Recently, transluminal prostheses have been widely used in the medical arts for implantation in blood vessels, biliary ducts, or other similar organs of the living body. These prostheses are commonly known as stents and are used to maintain, open, or dilate tubular structures. An example of a commonly used stent is given in U.S. Pat. No. 4,733,665 filed by Palmaz on Nov. 7, 1985, which is hereby incorporated herein by reference. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon application of a radially, outwardly directed force, by the balloon catheter, from the interior of the tubular shaped member.

However, one concern with such stents is that they are often impractical for use in some vessels such as the carotid artery. The carotid artery is easily accessible from the exterior of the human body, and is close to the surface of the skin. A patient having a balloon expandable stent made from stainless steel or the like, placed in their carotid artery, might be susceptible to severe injury through day to day activity.

A sufficient force placed on the patient's neck could cause the stent to collapse, resulting in injury to the patient. In order to prevent this, self-expanding stents have been proposed for use in such vessels. Self-expanding stents act like springs and will recover to their expanded or implanted configuration after being crushed.

One type of self-expanding stent is disclosed in U.S. Pat. No. 4,655,771, which stent has a radially and axially flexible, elastic tubular body with a predetermined diameter that is variable under axial movement of the ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprises an outer catheter for holding the stent at its distal end, and an inner piston which pushes the stent forward once it is in position.

However, braided stents have many disadvantages. They typically do not have the necessary radial strength to effectively hold open a diseased vessel. In addition, the plurality of wires or fibers used to make such stents could become dangerous if separated from the body of the stent, where they could pierce through the vessel. Therefore, there has been a desire to have a self-expanding stent which is cut from a tube of metal, which is the common manufacturing method for many commercially available balloon-expandable stents. In order to manufacture a self-expanding stent cut from a tube, the alloy used would preferably exhibit superelastic or psuedoelastic characteristics at body temperature, so that it is crush recoverable.

The prior art makes reference to the use of alloys such as Nitinol (Ni—Ti alloy), which have shape memory and/or superelastic characteristics, in medical devices which are designed to be inserted into a patient's body. The shape memory characteristics allow the devices to be deformed to facilitate their insertion into a body lumen or cavity and then be heated within the body so that the device returns to its original shape. Superelastic characteristics, on the other hand, generally allow the metal to be deformed and restrained in the deformed condition to facilitate the insertion of the medical device containing the metal into a patient's body, with such deformation causing the phase transformation. Once within the body lumen, the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable (the Af temperature). The shape of the metal during this heat treatment is the shape "remembered." The heat-treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase, and during this phase transformation the metal reverts back to its original shape if unrestrained. If restrained, the metal will remain martensitic until the restraint is removed.

Methods of using the shape memory characteristics of these alloys in medical devices intended to be placed within a patient's body present operational difficulties. For example, with shape memory alloys having a stable martensite temperature below body temperature, it is frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices can be introduced into a patient's body with little or no problem, but they must be heated to the martensite-to-austenite transformation temperature which is frequently high enough to cause tissue damage.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load, and to recover from the deformation upon the removal of the load, is commonly referred to as superelasticity or pseudoelasticity. It is this property of the material which makes it useful in manufacturing tube cut self-expanding stents.

The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.). However, the prior art has yet to disclose any suitable tube-cut self-expanding stents. In addition, many of the prior art stents lacked the necessary rigidity or hoop strength to keep the body vessel open. In addition, many of the prior art stents have large openings at their expanded diameter. The smaller the openings are on an expanded stent, the more plaque or other deposits it can trap between the stent and the vessel wall. Trapping these deposits is important to the continuing health of the patient in that it helps prevent plaque prolapse into the vessel, restenosis of the vessel it is implanted into, and strokes caused by the release of embolic particles into the bloodstream.

One additional concern with stents, and with other medical devices, is that they may exhibit reduced radiopacity under X-ray fluoroscopy. To overcome this problem, it is common practice to attach markers made from highly radiopaque materials to the stent, or to use radiopaque materials in plating or coating processes. Those materials are typically gold, platinum, or tantalum. The prior art makes reference to these markers or processes in U.S. Pat. No. 5,632,771 (Boatman et al), U.S. Pat. No. 6,022,374 (Imran), U.S. Pat. No. 5,741,327 (Frantzen), U.S. Pat. No. 5,725,572 (Lam et al), and U.S. Pat. No. 5,800,526 (Anderson et al). However, due to the relative position of these materials in the galvanic series versus the position of the base metal of the stent in the galvanic series, there is a certain challenge to overcome; namely, that of galvanic corrosion.

SUMMARY OF THE INVENTION

The present invention provides for a self-expanding tube cut stent which overcomes many of the disadvantages associated with the prior art stents. Also, the present invention overcomes many of the disadvantages associated with reduced radiopacity exhibited by self-expanding stents, balloon-expandable stents, and other medical devices.

In accordance with one aspect, the present invention is directed to a stent comprising a thin-walled tubular member, with front and back open ends, and having a first diameter for insertion into a vessel and a second diameter for deployment within the vessel. The stent also comprises at least one radiopaque tab mounted to at least one of the front and back open ends, which is micro-alloyed from a combination of materials to improve the radiopacity of the stent, without creating a significant galvanic element.

In accordance with another aspect, the present invention is directed to a stent, comprising a thin-walled tubular member, made from a superelastic Nickel Titanium alloy, with front and back open ends, and having a first diameter for insertion into a vessel and a second diameter for deployment within the vessel. The stent also comprises at least one tab mounted to at least one of the front and back open ends, which is micro-alloyed from a combination of materials to improve the radiopacity of the stent, without creating a significant galvanic element.

In accordance with another aspect, the present invention is directed to a method of micro-alloying a combination of alloys on a portion of a medical device to improve the radiopacity of the medical device under X-ray fluoroscopy, without creating a significant galvanic element.

In accordance with another aspect, the present invention is directed to a stent, comprising a thin-walled tubular member, with front and back open ends, and having a first diameter for insertion into a vessel and a second diameter for deployment within the vessel. The stent also comprises at least one radiopaque tab mounted to the thin-walled tubular member, which is micro-alloyed from a combination of materials to improve the radiopacity of the stent, without creating a significant galvanic element.

In accordance with another aspect, the present invention is directed to a stent, comprising a thin-walled tubular member, made from a superelastic Nickel Titanium alloy, with front and back open ends, and having a first diameter for insertion into a vessel and a second diameter for deployment within the vessel. The stent also comprises at least one radiopaque tab mounted to the thin-walled tubular member, which is micro-alloyed from a combination of materials to improve the radiopacity of the stent, without creating a significant galvanic element.

The advantages of micro-alloying a combination of materials, including a radiopaque material, on a medical device are that more precise placement of the device can be achieved under X-ray fluoroscopy, the device can be visualized post-procedurally, and the possibility of galvanic action between the alloys on the device is substantially eliminated.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE PREFERRED EMBODIMENTS

Figure 3:
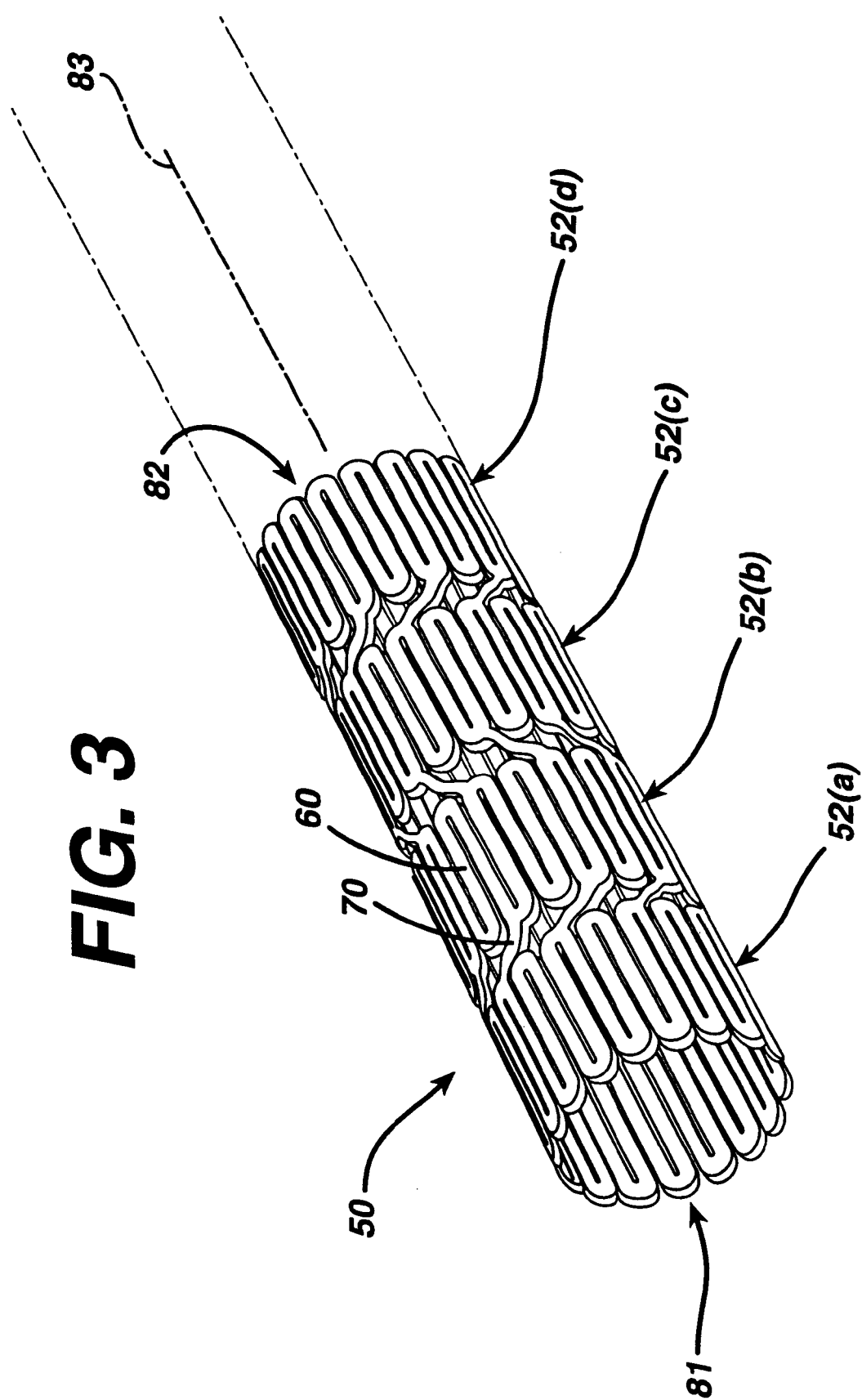
FIG. 3 is a perspective view of a stent made in accordance with the present invention, showing the stent in its compressed state.
Figure 4:
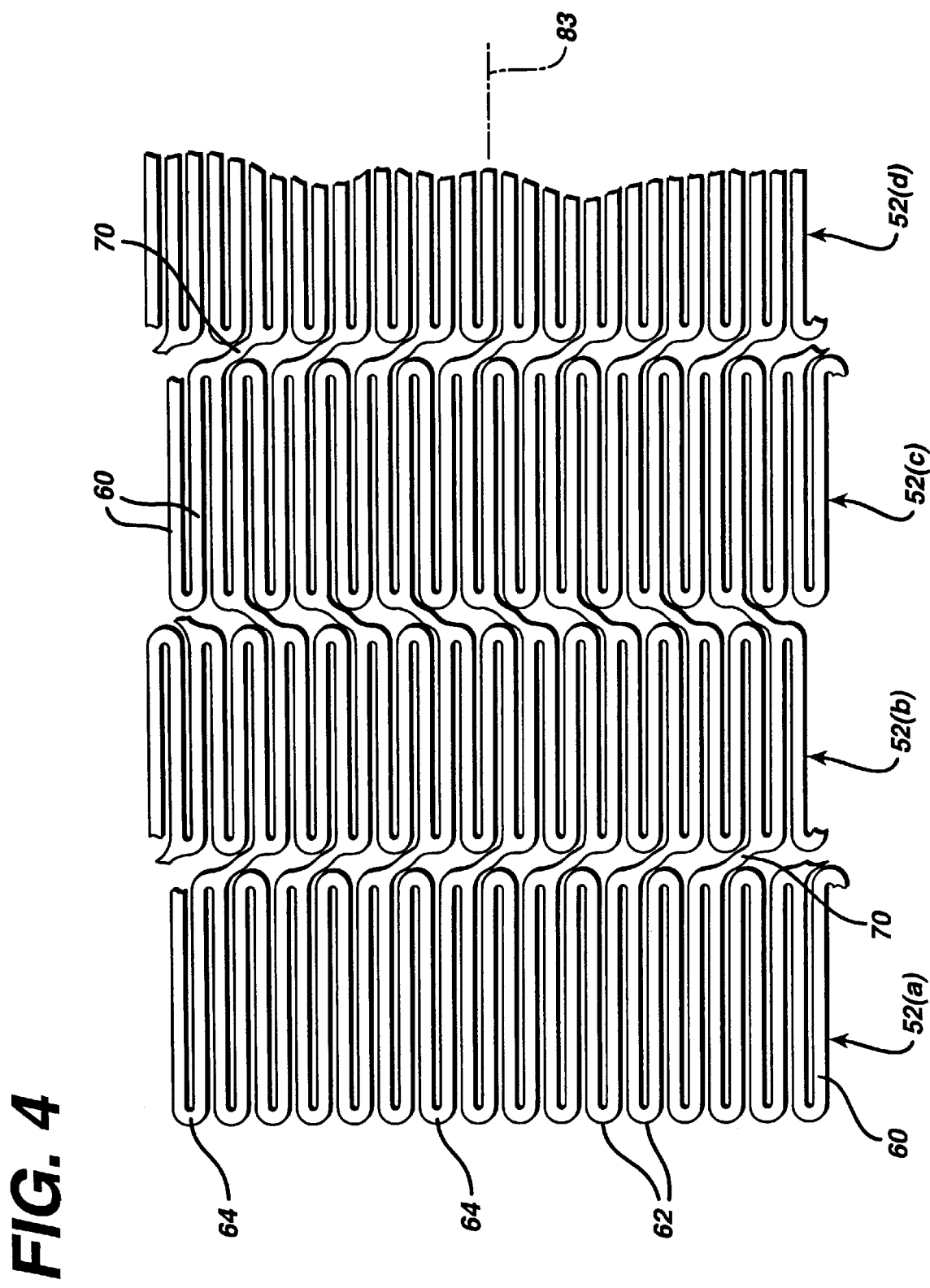
FIG. 4 is a sectional, flat view of the stent shown in FIG. 1.

While the present invention may be used on any number of medical devices, including stents, for ease of explanation, one exemplary embodiment of the invention with respect to self-expanding Nitinol stents will be described in detail. Referring to the figures wherein like numerals indicate the same element throughout the views, there is shown in FIGS. 3 and 4, a stent 50 made in accordance with the present invention. FIGS. 3 and 4 show stent 50 in its un-expanded or compressed state. Stent 50 is preferably made from a superelastic alloy such as Nitinol. Most preferably, stent 50 is made from an alloy comprising from about 50.5% (as used herein these percentages refer to atomic percentages) Ni to about 60% Ni, and more preferably about 55% Ni, with the remainder of the alloy Ti. Preferably, the stent is such that it is superelastic at body temperature, and preferably has an Af in the range from about 24° C. to about 37° C. The superelastic design of the stent makes it crush recoverable which, as discussed above, makes it useful as a stent or frame for any number of vascular devices in different applications.

Figure 1:
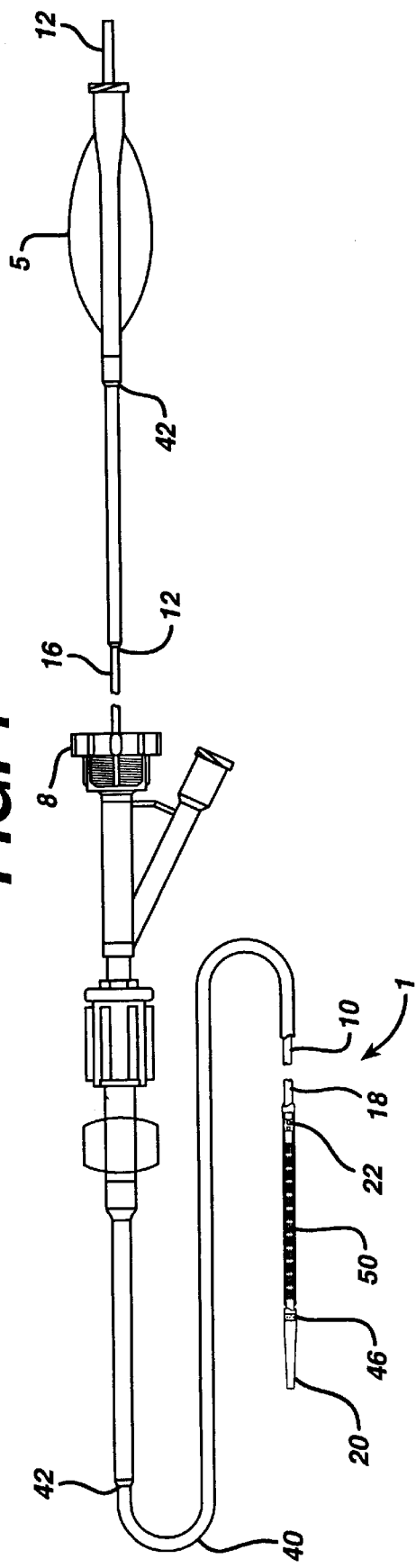
FIG. 1 is a simplified partial cross-sectional view of a stent delivery apparatus having a stent loaded therein, which can be used with a stent made in accordance with the present invention.

Stent 50 is a tubular member having front and back open ends 81 and 82 and a longitudinal axis 83 extending therebetween. The tubular member has a first smaller diameter, FIGS. 3 and 4, for insertion into a patient and navigation through the vessels, and a second larger diameter, FIGS. 5 and 6, for deployment into the target area of a vessel. The tubular member is made from a plurality of adjacent hoops 52, FIG. 1 showing hoops 52(a)–52(b), extending between the front and back ends 81 and 82. The hoops 52 include a plurality of longitudinal struts 60 and a plurality of loops 62 connecting adjacent struts, wherein adjacent struts are connected at opposite ends so as to form an S or Z shape pattern. The loops 62 are curved, substantially semi-circular and symmetrical sections about their centers 64.

Stent 50 further includes a plurality of bridges 70 which connect adjacent hoops 52 which can best be described by referring to FIG. 4. Each bridge has two ends 56 and 58. The bridges have one end attached to one strut and/or loop, and another end attached to a strut and/or loop on an adjacent hoop. Bridges 70 connect adjacent struts together at bridge to loop connection points 72 and 74. For example, end 56 is connected to loop 64(a) at bridge to loop connection point 72, and end 58 is connected to loop 64(b) at bridge to loop connection point 74. Each bridge to loop connection point has center 76. The bridge to loop connection points are separated angularly with respect to the longitudinal axis. That is, the connection points are not immediately opposite each other. Essentially, one could not draw a straight line between the connection points, wherein such line would be parallel to the longitudinal axis of the stent.

The above described geometry helps to better distribute strain throughout the stent, prevents metal to metal contact when the stent is bent, and minimizes the opening size between the features, struts loops and bridges. The number of and nature of the design of the struts, loops and bridges are important factors when determining the working properties and fatigue life properties of the stent. It was previously thought that in order to improve the rigidity of the stent, that struts should be large, and therefore there should be fewer struts per hoop. However, it has now been discovered that stents having smaller struts and more struts per hoop actually improve the construction of the stent and provide greater rigidity. Preferably, each hoop has between 24 to 36 or more struts. It has been determined that a stent having a ratio of number of struts per hoop to strut length L (in inches) which is greater than 400 has increased rigidity over prior art stents, which typically have a ratio of under 200. The length of a strut is measured in its compressed state parallel to the longitudinal axis 83 of the stent.

Figure 5:
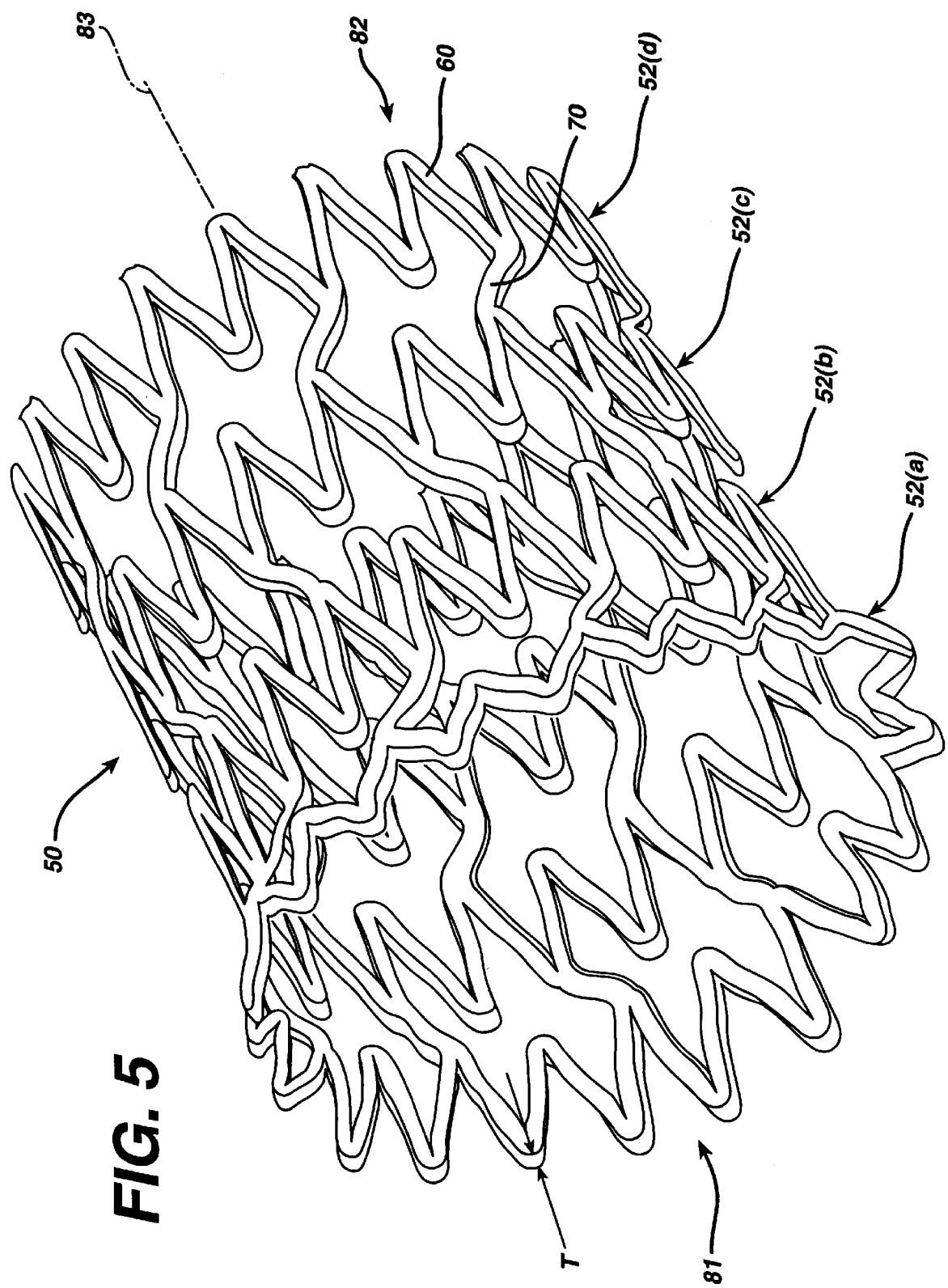
FIG. 5 is a perspective view of the stent shown in FIG. 1 but showing it in its expanded state.
Figure 6:
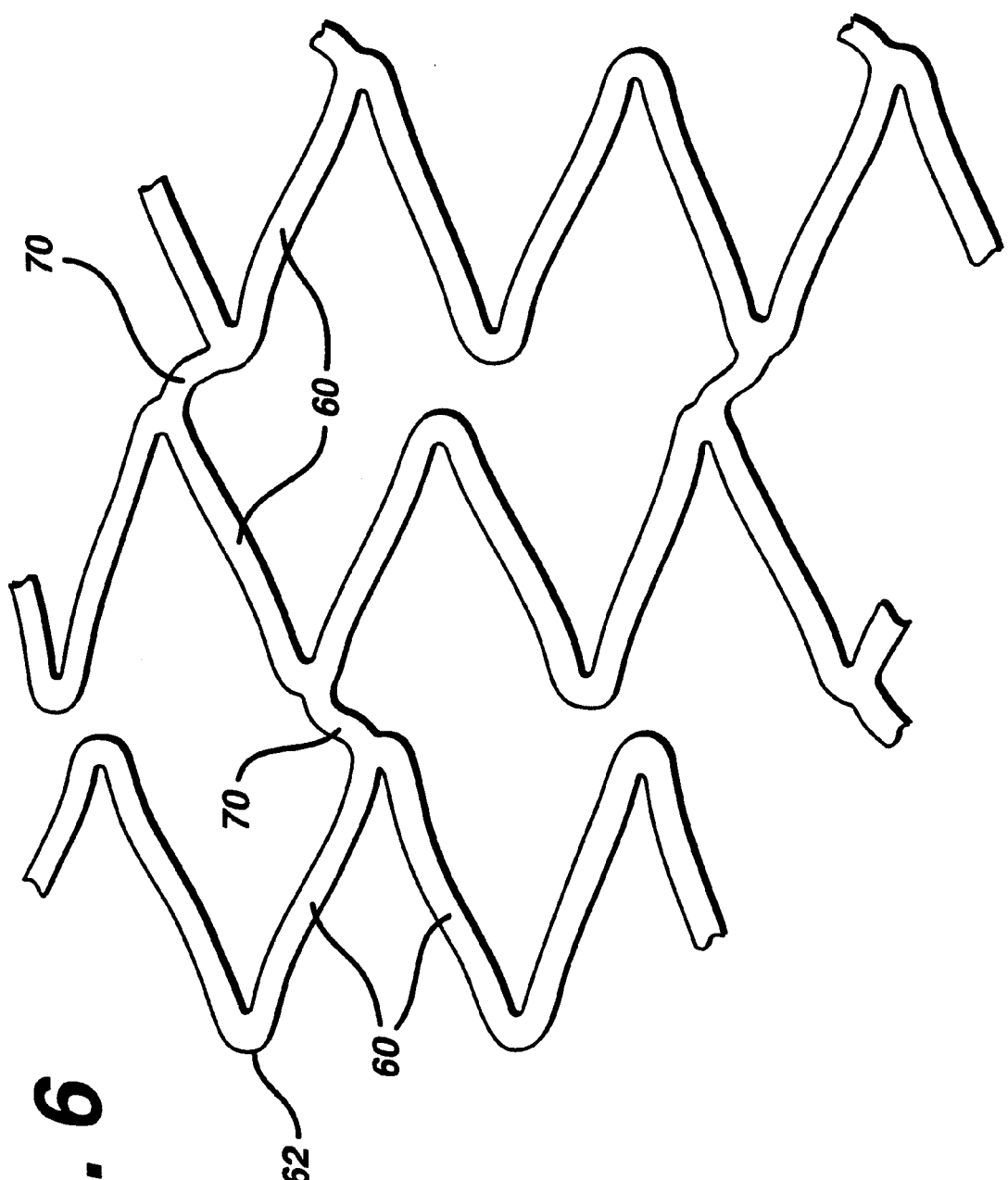
FIG. 6 is an enlarged sectional view of the stent shown in FIG. 5.

As seen from FIGS. 4 and 5, the geometry of the stent changes quite significantly as a stent is deployed from its un-expanded state to its expanded state. As a stent undergoes diametric change, the strut angle and strain levels in the loops and bridges are affected. Preferably, all of the stent features will strain in a predictable manor so that the stent is reliable and uniform in strength. In addition, it is preferable to minimize the maximum strain experienced by struts loops and bridges, since Nitinol properties are more generally limited by strain rather than by stress. As will be discussed in greater detail below, the stent sits in the delivery system in its un-expanded state as shown in FIG. 3. As the stent is deployed, it is allowed to expand towards its expanded state, as shown in FIG. 5, which preferably has a diameter which is the same or larger than the diameter of the target vessel.

Nitinol stents made from wire deploy in much the same manner, and are dependent upon the same design constraints, as laser cut stents. Stainless steel stents deploy similarly in terms of geometric changes as they are assisted by forces from balloons or other devices.

In trying to minimize the maximum strain experienced by features, the present invention utilizes structural geometries which distribute strain to areas of the stent which are less susceptible to failure than others. For example, one of the most vulnerable areas of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge connection points. One way to accomplish this is to utilize the largest possible radii while maintaining feature widths which are consistent with applied forces. Another consideration is to minimize the maximum open area of the stent. Efficient utilization of the original tube from which the stent is cut increases stent strength and its ability to trap embolic material.

Many of these design objectives have been accomplished by an exemplary embodiment of the present invention, shown in FIGS. 3 and 4. As seen from these figures, the most compact designs which maintain the largest radii at the loop to bridge connections are non-symmetric with respect to the centerline of the strut connecting loop. That is, loop to bridge connection point centers 76 are offset from the center 64 of the loops 62 to which they are attached. This feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

Figure 4A:
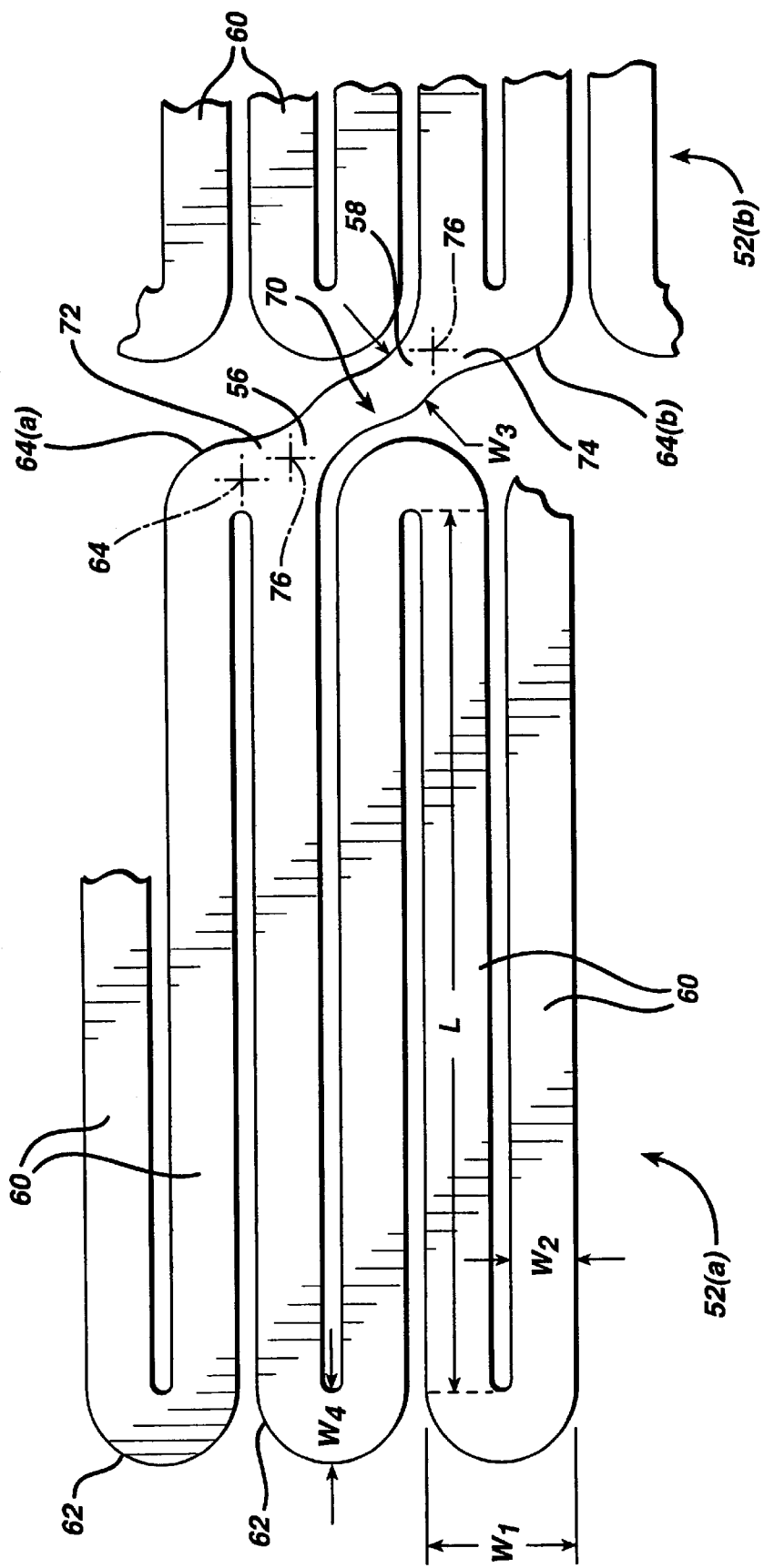
FIG. 4A is an enlarged view of section of the stent shown in FIG. 4.

As seen in FIG. 4A, stent 50 comprises strut connecting loops 62 having a width W4, as measured at the center 64 parallel to axis 83, which are greater than the strut widths W2, as measured perpendicular to axis 83 itself. In fact, it is preferable that the thickness of the loops vary so that they are thickest near their centers. This increases strain deformation at the strut and reduces the maximum strain levels at the extreme radii of the loop. This reduces the risk of stent failure and allows one to maximize radial strength properties. This feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

As mentioned above, bridge geometry changes as a stent is deployed from its compressed state to its expanded state and vise-versa. As a stent undergoes diametric change, strut angle and loop strain is affected. Since the bridges are connected to either the loops, struts or both, they are affected. Twisting of one end of the stent with respect to the other, while loaded in the stent delivery system, should be avoided. Local torque delivered to the bridge ends displaces the bridge geometry. If the bridge design is duplicated around the stent perimeter, this displacement causes rotational shifting of the two loops being connected by the bridges. If the bridge design is duplicated throughout the stent, as in the present invention, this shift will occur down the length of the stent. This is a cumulative effect as one considers rotation of one end with respect to the other upon deployment. A stent delivery system, such as the one described below, will deploy the distal end first, then allow the proximal end to expand. It would be undesirable to allow the distal end to anchor into the vessel wall while holding the stent fixed in rotation, then release the proximal end. This could cause the stent to twist or whip in rotation to equilibrium after it is at least partially deployed within the vessel. Such whipping action may cause damage to the vessel.

However, one exemplary embodiment of the present invention, as shown in FIGS. 3 and 4, reduces the chance of such events happening when deploying the stent. By mirroring the bridge geometry longitudinally down the stent, the rotational shift of the Z-sections may be made to alternate and will minimize large rotational changes between any two points on a given stent during deployment or constraint. That is, the bridges connecting loop 52(b) to loop 52(c) are angled upwardly from left to right, while the bridges connecting loop 52(c) to loop 52(d) are angled downwardly from left to right. This alternating pattern is repeated down the length of the stent. This alternating pattern of bridge slopes improves the torsional characteristics of the stent so as to minimize any twisting or rotation of the stent with respect to any two hoops. This alternating bridge slope is particularly beneficial if the stent starts to twist in vivo. As the stent twists, the diameter of the stent will change. Alternating bridge slopes tend to minimize this effect. The diameter of a stent having bridges which are all sloped in the same direction will tend to grow if twisted in one direction and shrink if twisted in the other direction. With alternating bridge slopes this effect is minimized and localized.

The feature is particularly advantageous for stents having large expansion ratios, which in turn requires them to have extreme bending requirements where large elastic strains are required. Nitinol, as stated above, can withstand extremely large amounts of elastic strain deformation, so the above features are well suited to stents made from this alloy. This feature allows for maximum utilization of Ni—Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

Preferably, stents are laser cut from small diameter tubing. For prior art stents, this manufacturing process led to designs with geometric features, such as struts, loops and bridges, having axial widths W2, W4 and W3 (respectively) which are larger than the tube wall thickness T (shown in FIG. 5). When the stent is compressed, most of the bending occurs in the plane that is created if one were to cut longitudinally down the stent and flatten it out. However, for the individual bridges, loops and struts, which have widths greater than their thickness, there is a greater resistance to this in-plane bending than to out-of-plane bending. Because of this, the bridges and struts tend to twist, so that the stent as a whole may bend more easily. This twisting is a buckling condition which is unpredictable and can cause potentially high strain.

However, this problem has been solved in an exemplary embodiment of the present invention, as shown in FIGS. 3 and 4. As seen from these figures, the widths of the struts, hoops and bridges are equal to or less than the wall thickness of the tube. Therefore, substantially all bending and, therefore, all strains are "out-of-plane." This minimizes twisting of the stent which minimizes or eliminates buckling and unpredictable strain conditions. This feature is particularly advantageous for stents having large expansion ratios, which in turn requires them to have extreme bending requirements where large elastic strains are required. Nitinol, as stated above, can withstand extremely large amounts of elastic strain deformation, so the above features are well suited to stents made from this alloy. This feature allows for maximum utilization of Ni—Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

Figure 7:
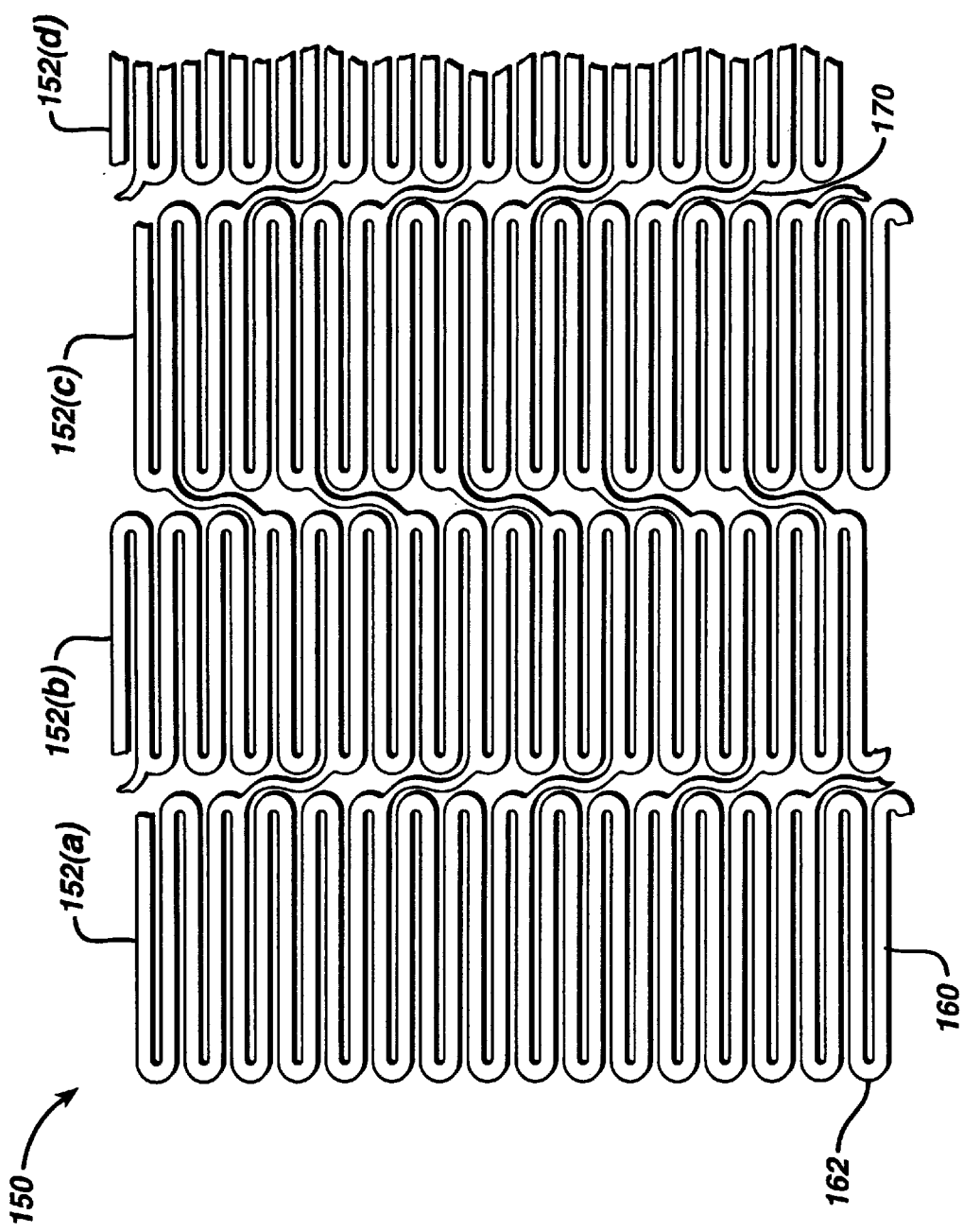
FIG. 7 is a view similar to that of FIG. 4 but showing an alternative embodiment of the present invention.

An alternate exemplary embodiment of the present invention is shown in FIG. 7. FIG. 7 shows stent 150 which is similar to stent 50 shown in the previous drawings. Stent 150 is made from a plurality of adjacent hoops 152, FIG. 7 showing hoops 152(*a*)–152(*d*). The hoops 152 include a plurality of longitudinal struts 160 and a plurality of loops 162 connecting adjacent struts, wherein adjacent struts are connected at opposite ends so as to form an S or Z shape pattern. Stent 150 further includes a plurality of bridges 170 which connect adjacent hoops 152. As seen from the figure, bridges 170 are non-linear and curve between adjacent hoops. Having curved bridges allows the bridges to curve around the loops and struts so that the hoops can be placed closer together which in turn, minimizes the maximum open area of the stent and increases its radial strength as well. This can best be explained by referring to FIG. 6. The above described stent geometry attempts to minimize the largest circle which could be inscribed between the bridges, loops and struts, when the stent is expanded. Minimizing the size of this theoretical circle, greatly improves the stent because it is then better suited to trap embolic material once it is inserted into the patient.

As mentioned above, it is preferred that the stent of the present invention be made from a superelastic alloy and most preferably made of an alloy material having greater than 50.5 atomic % Nickel and the balance titanium. Greater than 50.5 atomic % Nickel allows for an alloy in which the temperature at which the martensite phase transforms completely to the austenite phase (the Af temperature) is below human body temperature, and preferably is about 24° C. to about 37° C., so that austenite is the only stable phase at body temperature.

In manufacturing the Nitinol stent, the material is first in the form of a tube. Nitinol tubing is commercially available from a number of suppliers including Nitinol Devices and Components, Fremont Calif. The tubular member is then loaded into a machine which will cut the predetermined pattern of the stent into the tube, as discussed above and as shown in the figures. Machines for cutting patterns in tubular devices to make stents or the like are well known to those of ordinary skill in the art and are commercially available. Such machines typically hold the metal tube between the open ends while a cutting laser, preferably under microprocessor control, cuts the pattern. The pattern dimensions and styles, laser positioning requirements, and other information are programmed into a microprocessor which controls all aspects of the process. After the stent pattern is cut, the stent is treated and polished using any number of methods or combination of methods well known to those skilled in the art. Lastly, the stent is then cooled until it is completely martensitic, crimped down to its un-expanded diameter and then loaded into the sheath of the delivery apparatus.

Figure 8:
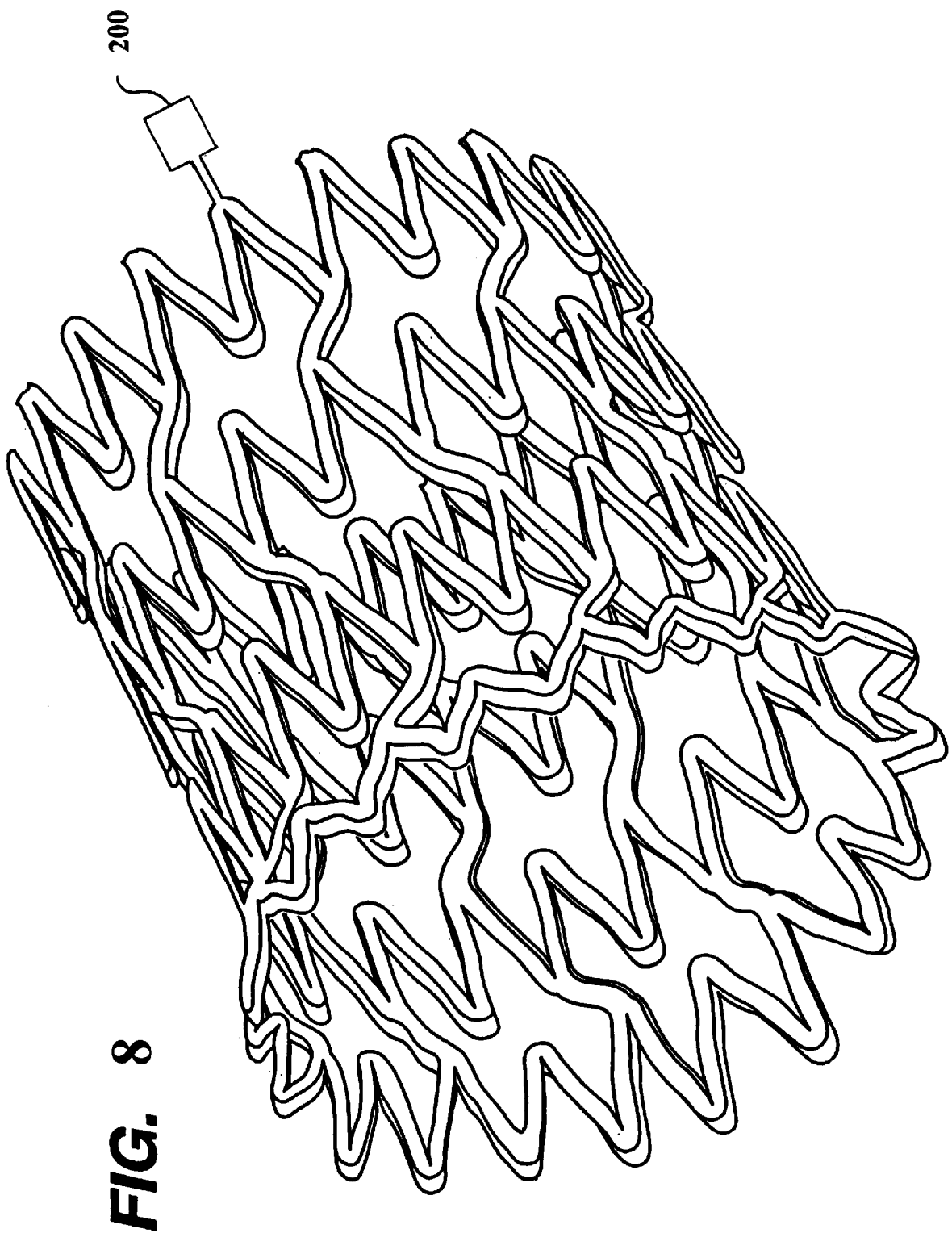
FIG. 8 is an enlarged sectional view of the end of a stent including a tab, after cutting.
Figure 9:
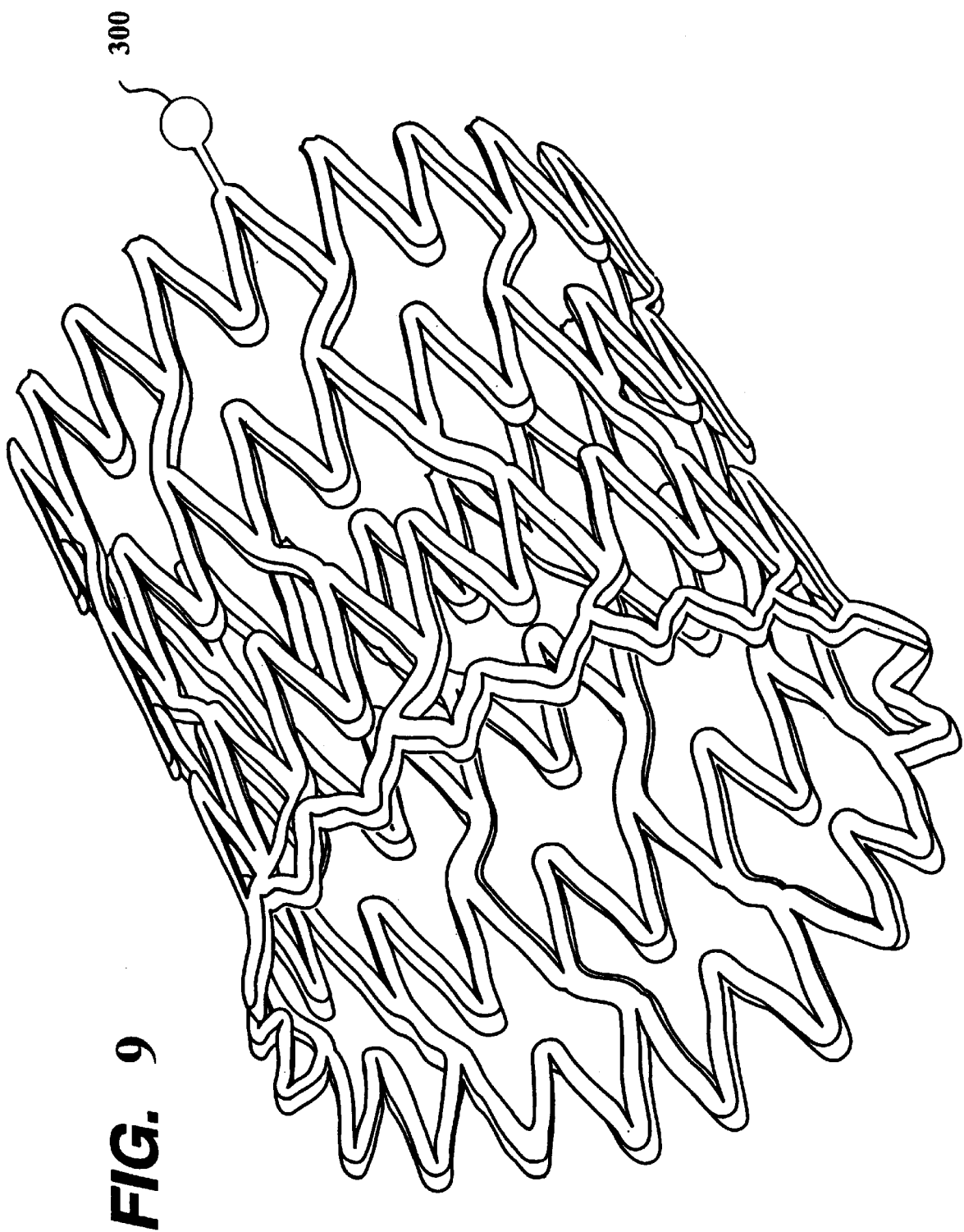
FIG. 9 is a view similar to that of FIG. 8, but showing a tab after melting and micro-alloying with a radiopaque alloy.

Referring to FIG. 8, there is illustrated another exemplary embodiment of the present invention. In this exemplary embodiment, the cutting pattern of the stent includes at least one tab or marker 200 attached to the loops at the front and back ends of the stent. These tabs may be formed from any suitable material, and are preferably formed from a highly radiopaque material to assist in positioning the stent within the lumen of the vessel. In this embodiment, it is suggested to "micro-alloy" a radiopaque material like gold, platinum, tantalum, niobium, molybdenum, rhodium, palladium, silver, hafnium, tungsten or iridium with the Nickel Titanium at specific locations and on specific features of the stent, for example tabs 200. Once the predetermined pattern is cut into the tubular member, as described above, in a secondary process, performed in a protective atmosphere or under vacuum, the tabs 200 or other features may selectively be melted by the application of heat from a source, while a predetermined amount of the radiopaque material is added. Means for applying this heat may include devices such as lasers, induction heating, electric arc melting, resistance heating and electron beam melting, and are well known to those of ordinary skill in the art, and are commercially available. Through surface tension, the molten pool will form a sphere, 300, as illustrated in FIG. 9. The sphere remains attached to the device upon solidification. The sphere includes a micro-alloy of Nickel Titanium and a radiopaque alloy chosen from a group consisting of gold, platinum, tantalum, niobium, molybdenum, rhodium, palladium, silver, hafnium, tungsten and iridium, while the chemical composition of the balance of the device remains unchanged. The resulting Nickel Titanium alloy has a much reduced tendency to create a galvanic element with the binary Nickel Titanium.

Figure 2:
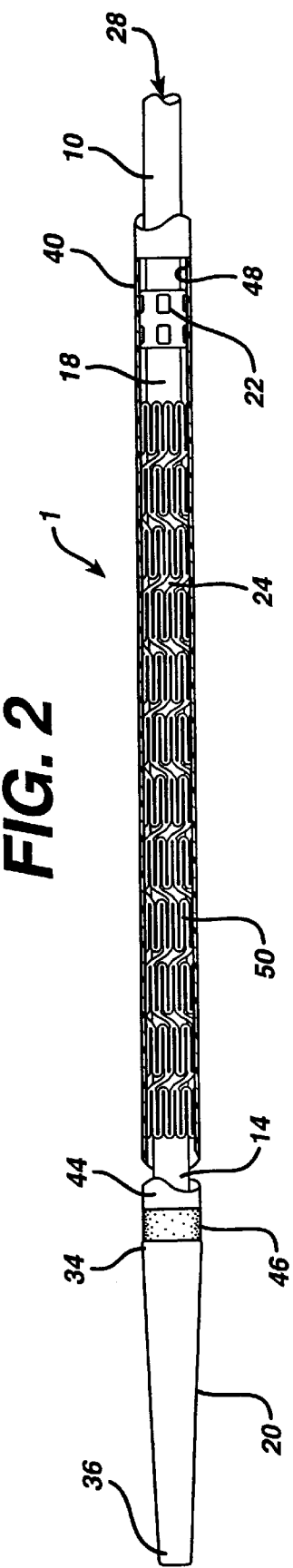
FIG. 2 is a view similar to that of FIG. 1 but showing an enlarged view of the distal end of the apparatus.

It is believed that many of the advantages of the present invention can be better understood through a brief description of a delivery apparatus for the stent, as shown in FIGS. 1 and 2. FIGS. 1 and 2 show a self-expanding stent delivery apparatus 1 for a stent made in accordance with the present invention. Apparatus 1 comprises inner and outer coaxial tubes. The inner tube is called the shaft 10 and the outer tube is called the sheath 40. Shaft 10 has proximal and distal ends 12 and 14 respectively. The distal end 14 of the shaft terminates at a luer lock hub 5. Preferably, shaft 10 has a proximal portion 16 which is made from a relatively stiff material such as stainless steel, Nitinol, or any other suitable material, and a distal portion 18 which may be made from a polyethylene, polyimide, pellethane, Pebax, Vestamid, Cristamid, Grillamid or any other suitable material known to those of ordinary skill in the art. The two portions are joined together by any number of means known to those of ordinary skill in the art. The stainless steel proximal end gives the shaft the necessary rigidity or stiffness it needs to effectively push out the stent, while the polymeric distal portion provides the necessary flexibility to navigate tortuous vessels.

The distal portion 18 of the shaft has a distal tip 20 attached thereto. The distal tip 20 has a proximal end 34 whose diameter is substantially the same as the outer diameter of the sheath 40. The distal tip tapers to a smaller diameter from its proximal end to its distal end, wherein the distal end 36 of the distal tip has a diameter smaller than the inner diameter of the sheath. Also attached to the distal portion 18 of shaft 10 is a stop 22 which is proximal to the distal tip 20. Stop 22 may be made from any number of materials known in the art, including stainless steel, and is even more preferably made from a highly radiopaque material such as platinum, gold or tantalum. The diameter of stop 22 is substantially the same as the inner diameter of sheath 40, and would actually make frictional contact with the inner surface of the sheath. Stop 22 helps to push the stent out of the sheath during deployment, and helps the stent from migrating proximally into the sheath 40.

A stent bed 24 is defined as being that portion of the shaft between the distal tip 20 and the stop 22. The stent bed 24 and the stent 50 are coaxial so that the portion of shaft 18 comprising the stent bed 24 is located within the lumen of the stent 50. However, the stent bed 24 does not make any contact with stent 50 itself. Lastly, shaft 10 has a guidewire lumen 28 extending along its length from its proximal end 12 and exiting through its distal tip 20. This allows the shaft 10 to receive a guidewire much in the same way that an ordinary balloon angioplastly catheter receives a guidewire. Such guidewires are well known in art and help guide catheters and other medical devices through the vasculature of the body.

Sheath 40 is preferably a polymeric catheter and has a proximal end 42 terminating at a hub 52. Sheath 40 also has a distal end 44 which terminates at the proximal end 34 of distal tip 20 of the shaft 18, when the stent is in its fully un-deployed position as shown in the figures. The distal end 44 of sheath 40 includes a radiopaque marker band 46 disposed along its outer surface. As will be explained below, the stent is fully deployed when the marker band 46 is lined up with radiopaque stop 22, thus indicating to the physician that it is now safe to remove the apparatus 1 from the body. Sheath 40 preferably comprises an outer polymeric layer and an inner polymeric layer. Positioned between outer and inner layers is a braided reinforcing layer. Braided reinforcing layer is preferably made from stainless steel. The use of braided reinforcing layers in other types of medical devices can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19, 1993, all of which are hereby incorporated herein by reference.

FIGS. 1 and 2 show the stent 50 as being in its fully un-deployed position. This is the position the stent is in when the apparatus 1 is inserted into the vasculature and its distal end is navigated to a target site. Stent 50 is disposed around stent bed 24 and at the distal end 44 of sheath 40. The distal tip 20 of the shaft 10 is distal to the distal end 44 of the sheath 40, and the proximal end 12 of the shaft 10 is proximal to the proximal end 42 of the sheath 40. The stent 50 is in a compressed state and makes frictional contact with the inner surface 48 of the sheath 40.

When being inserted into a patient, sheath 40 and shaft 10 are locked together at their proximal ends by a Touhy Borst valve 8. This prevents any sliding movement between the shaft and sheath which could result in a premature deployment or partial deployment of the stent 50. When the stent 50 reaches its target site and is ready for deployment, the Touhy Borst valve 8 is opened so that that the sheath 40 and shaft 10 are no longer locked together.

The method under which the apparatus 1 deploys the stent 50 is readily apparent. The apparatus 1 is first inserted into a vessel so that the stent bed 24 is at a target lesion site. Once this has occurred the physician would open the Touhy Borst valve 8. The physician would then grasp the proximal end 12 of shaft 10 so as to hold it in place. Thereafter, the physician would grasp the proximal end 42 of sheath 40 and slide it proximal, relative to the shaft 40. Stop 22 prevents the stent 50 from sliding back with the sheath 40, so that as the sheath 40 is moved back, the stent 50 is pushed out of the distal end 44 of the sheath 40. Stent deployment is complete when the radiopaque band 46 on the sheath 40 is proximal to radiopaque stop 22. The apparatus 1 can now be withdrawn through stent 50 and removed from the patient.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

That which is claimed is:

1. A stent, comprising:

a) a thin-walled tubular member having front and back open ends and having a first diameter for insertion into a vessel and a second diameter for deployment in said vessel; and b) at least one radiopaque tab mounted to at least one of said front and back open ends, said tab being integral to the thin-walled tubular member and comprising a micro-alloy structure, including a material from which the thin-walled tubular member is constructed and at least a second radiopaque material, said tab assuming a substantially spherical shape from the micro-alloy forming process.

2. The stent according to claim 1, wherein said stent is made from a superelastic alloy.

3. The stent according to claim 2, wherein said superelastic alloy comprises from about 50.5 percent to about 60 percent Nickel and the remainder comprising Titanium.

4. The stent according to claim 1, wherein said radiopaque alloy is chosen from a group consisting of gold, platinum, tantalum, niobium, molybdenum, rhodium, palladium, silver, hafnium, tungsten and iridium.

5. A stent, comprising:

a) a thin-walled tubular member, made from a superelastic Nickel Titanium alloy, having front and back open ends and having a first diameter for insertion into a vessel and a second diameter for deployment in said vessel; and b) at least one radiopaque tab mounted to least one of said front and back open ends, said tab being integral to the thin-walled tubular member and comprising a micro-alloy structure, including a material from which the thin-walled tubular member is constructed and at least a second, radiopaque material, said tab assuming a substantially spherical shape from the micro-alloy forming process.

6. The stent according to claim 5, wherein said superelastic alloy comprises from about 50.5 percent to about 60 percent Nickel and the remainder comprising Titanium.

7. The stent according to claim 5, wherein said radiopaque alloy is chosen from a group consisting of gold, platinum, tantalum, niobium, molybdenum, rhodiu, palladium, silver, hafnium, tungsten and iridium.

8. A stent, comprising:
  a) a thin-walled tubular member having front and back open ends and having a first diameter for insertion into a vessel and a second diameter for deployment in said vessel; and
  b) at least one radiopaque tab mounted to said thin-walled tubular member, said tab being integral to the thin-walled tubular member and comprising a micro-alloy structure, including a material from which the thin-walled tubular member is constructed and at least a second, radiopaque material, said tab assuming a substantially spherical shape from the micro-alloy forming process.

9. A stent, comprising:
  a) a thin-walled tubular member, made from a superelastic Nickel Titanium alloy, having front and back open ends and having a first diameter for insertion into a vessel and a second diameter for deployment in said vessel; and
  b) at least one radiopaque tab mounted to said thin-walled tubular member, said tab being integral to the thin-walled tubular member and comprising a micro-alloy structure, including a material from which the thin-walled tubular member is constructed and at least a second, radiopaque material, said tab assuming a substantially spherical shape from the micro-alloy forming process.

* * * * *